US008481334B1

(12) United States Patent
Saul

(10) Patent No.: US 8,481,334 B1
(45) Date of Patent: *Jul. 9, 2013

(54) METHOD OF ATTACHING A LIGAND TO A SOLID SUPPORT

(75) Inventor: Steven J. Saul, Arlington, MA (US)

(73) Assignee: Charm Sciences, Inc., Lawrence, MA (US)

( * ) Notice: Subject to any disclaimer, the term of this patent is extended or adjusted under 35 U.S.C. 154(b) by 649 days.

This patent is subject to a terminal disclaimer.

(21) Appl. No.: 12/080,044

(22) Filed: Mar. 31, 2008

Related U.S. Application Data

(62) Division of application No. 10/289,089, filed on Nov. 6, 2002, now abandoned.

(60) Provisional application No. 60/332,877, filed on Nov. 6, 2001.

(51) Int. Cl.
*G01N 33/543* (2006.01)
*C07K 1/00* (2006.01)

(52) U.S. Cl.
USPC ........... 436/518; 436/514; 436/525; 436/524; 436/538; 530/402; 530/816; 530/817; 530/820; 424/179.1; 422/61; 422/187; 422/188

(58) Field of Classification Search
USPC .......... 436/518, 525, 514, 524, 538; 530/402, 530/816, 817, 820; 424/179.1; 422/61, 187, 422/188
See application file for complete search history.

(56) References Cited

U.S. PATENT DOCUMENTS

| 4,172,094 | A | * | 10/1979 | Dybas et al. | ............ | 564/367 |
| 4,175,073 | A | * | 11/1979 | Carlsson et al. | ............ | 530/408 |
| 4,214,048 | A | | 7/1980 | Kitagawa | | |
| 4,472,301 | A | * | 9/1984 | Buckler et al. | ............ | 530/363 |
| 4,700,714 | A | | 10/1987 | Fuisz | | |

(Continued)

FOREIGN PATENT DOCUMENTS

| EP | 0 279 574 A1 | 8/1988 |
| EP | 0 291 176 B1 | 11/1988 |

(Continued)

OTHER PUBLICATIONS

Brady et al, Resistance Development Potential of Antibiotic/Antimicrobial Residue Levels Designated as "Safe Levels", Journal of Food Protection, 56(3):229-233, Mar. 1993, New Jersey, USA.

(Continued)

*Primary Examiner* — Mark Shibuya
*Assistant Examiner* — Pensee Do
(74) *Attorney, Agent, or Firm* — Richard J. Long; Leslie Meyer-Leon

(57) ABSTRACT

The invention features a method of attaching a ligand that has a free carboxyl group to a solid support by adding an amino group to the ligand to form a ligand-amino derivative, converting the ligand amino derivative to a ligand sulfhydryl derivative, attaching the ligand sulfhydryl derivative to a protein to form a ligand-linker-protein conjugate, and applying the ligand-linker-protein conjugate to the solid support. The method is particularly useful for immobilizing small molecule ligands having a free carboxyl group, such as cloxicillin, to a lateral-flow test strip, in order to make a detection zone on the test strip that exhibits a clear signal and enhanced sensitivity.

39 Claims, 6 Drawing Sheets

U.S. PATENT DOCUMENTS

| | | | |
|---|---|---|---|
| 4,703,017 A | 10/1987 | Campbell et al. | |
| 4,743,560 A | 5/1988 | Campbell et al. | |
| 4,826,759 A | 5/1989 | Guire et al. | |
| 4,849,337 A * | 7/1989 | Calenoff et al. | 435/7.92 |
| 4,999,285 A | 3/1991 | Stiso | |
| 5,096,837 A | 3/1992 | Fan et al. | |
| 5,238,652 A | 8/1993 | Sun et al. | |
| 5,260,222 A | 11/1993 | Patel et al. | |
| 5,266,497 A | 11/1993 | Imai et al. | |
| 5,296,347 A | 3/1994 | LaMotte, III | |
| 5,399,501 A * | 3/1995 | Pope et al. | 436/532 |
| 5,434,053 A | 7/1995 | Piasio | |
| 5,451,504 A | 9/1995 | Fitzpatrick et al. | |
| 5,521,102 A | 5/1996 | Boehringer et al. | |
| 5,545,721 A | 8/1996 | Carroll et al. | |
| 5,569,589 A | 10/1996 | Hiraoka et al. | |
| 5,591,645 A | 1/1997 | Rosenstein | |
| 5,602,040 A | 2/1997 | May et al. | |
| 5,622,871 A | 4/1997 | May et al. | |
| 5,656,448 A | 8/1997 | Kang et al. | |
| 5,656,502 A | 8/1997 | MacKay et al. | |
| 5,663,306 A * | 9/1997 | Aldwin et al. | 530/402 |
| 5,714,389 A | 2/1998 | Charlton et al. | |
| 5,726,010 A | 3/1998 | Clark | |
| 5,726,013 A | 3/1998 | Clark | |
| 5,739,041 A | 4/1998 | Nazareth et al. | |
| 5,753,517 A | 5/1998 | Brooks et al. | |
| 5,772,981 A * | 6/1998 | Govindan et al. | 424/1.49 |
| 5,846,800 A * | 12/1998 | Schlessinger et al. | 435/196 |
| 5,874,216 A | 2/1999 | Mapes | |
| 5,985,675 A | 11/1999 | Charm et al. | |
| 6,001,658 A | 12/1999 | Fredrickson | |
| D419,439 S | 1/2000 | Markovsky et al. | |
| 6,177,281 B1 | 1/2001 | Manita | |
| 6,319,466 B1 | 11/2001 | Markovsky et al. | |
| 6,475,805 B1 | 11/2002 | Charm et al. | |
| 6,524,804 B2 | 2/2003 | Degelaen et al. | |
| 7,396,689 B2 | 7/2008 | Dowd et al. | |
| 8,106,155 B2 | 1/2012 | Degelaen et al. | |

FOREIGN PATENT DOCUMENTS

| | | | |
|---|---|---|---|
| EP | 0 291 194 B1 | 11/1988 | |
| EP | 0 299 428 A2 | 1/1989 | |
| EP | 0 306 336 B1 | 3/1989 | |
| EP | 0 321 145 A2 | 6/1989 | |
| EP | 0 378 391 B1 | 7/1990 | |
| EP | 0 516 095 A2 | 12/1992 | |
| EP | 0 582 231 A1 | 2/1994 | |
| EP | 0 593 112 B1 | 4/1994 | |
| EP | 0 284 232 B1 | 6/1995 | |
| WO | WO 90/15327 | 12/1990 | |
| WO | WO 94/02850 | 2/1994 | |
| WO | WO 94/23300 | 10/1994 | |
| WO | WO 96/38720 | 12/1996 | |
| WO | WO 97/03209 | 1/1997 | |
| WO | WO 97/05287 | 2/1997 | |
| WO | WO 99/04267 | 1/1999 | |
| WO | WO 99/34191 | 7/1999 | |
| WO | WO 0210708 A2 | 2/2002 | |

OTHER PUBLICATIONS

Charm et al, An Integrated System Monitoring Milk for FDA "Safe Levels" Using Charm Test Methods, Journal of the Association of Food and Drug Officials, 58(1), 17-29, Jan. 1994, Malden, MA USA.

Charm et al, Microbial Receptor Assay for Rapid Detection and Identification of Seven Families of Antimicrobial Drugs in Milk: Collaborative Study, J.Assoc. Off.Anal. Chem. 71(2), 1988, Malden, MA USA.

Hassnoot et al, Evaluation of a Sol Particle Immunoassay (SPIA) Based Single-Step Strip Test for the Detection of Sulfadimidine Residues, EuroResidue III (1996), 461-465, The Netherlands.

A Short Guide—Developing Immunochromatographic Test Strips, 1996, Lit No. TB500, Millipore Corporation, Bedford, MA, USA.

Verheijen et al, Single-Step Tests for Residue Analyses, DLO State Institue for Quality Control of Agricultural Products (RIKILT-DLO), Jun. 3, 1998, The Netherlands.

Wong, Chemistry of Protein Conjugation and Cross-Linking, Univ. of Texas Health Center, 39-40, 1991, Boca Raton, FL, USA.

Wong, Chemistry of Protein Conjugation and Cross-Linking, Univ. of Texas Health Center, 122-123, 1991, Boca Raton, FL, USA.

Wong, Chemistry of Protein Conjugation and Cross-Linking, Univ. of Texas Health Center, 195-204, 1991, Boca Raton, FL, USA.

Hermanson et al, Immobilized Affinity Ligand Techniques, 98-110, 1992, San Diego, California, USA.

Hernanson, Bioconjugate Techniques, 169-186, San Diego, CA, USA.

\* cited by examiner

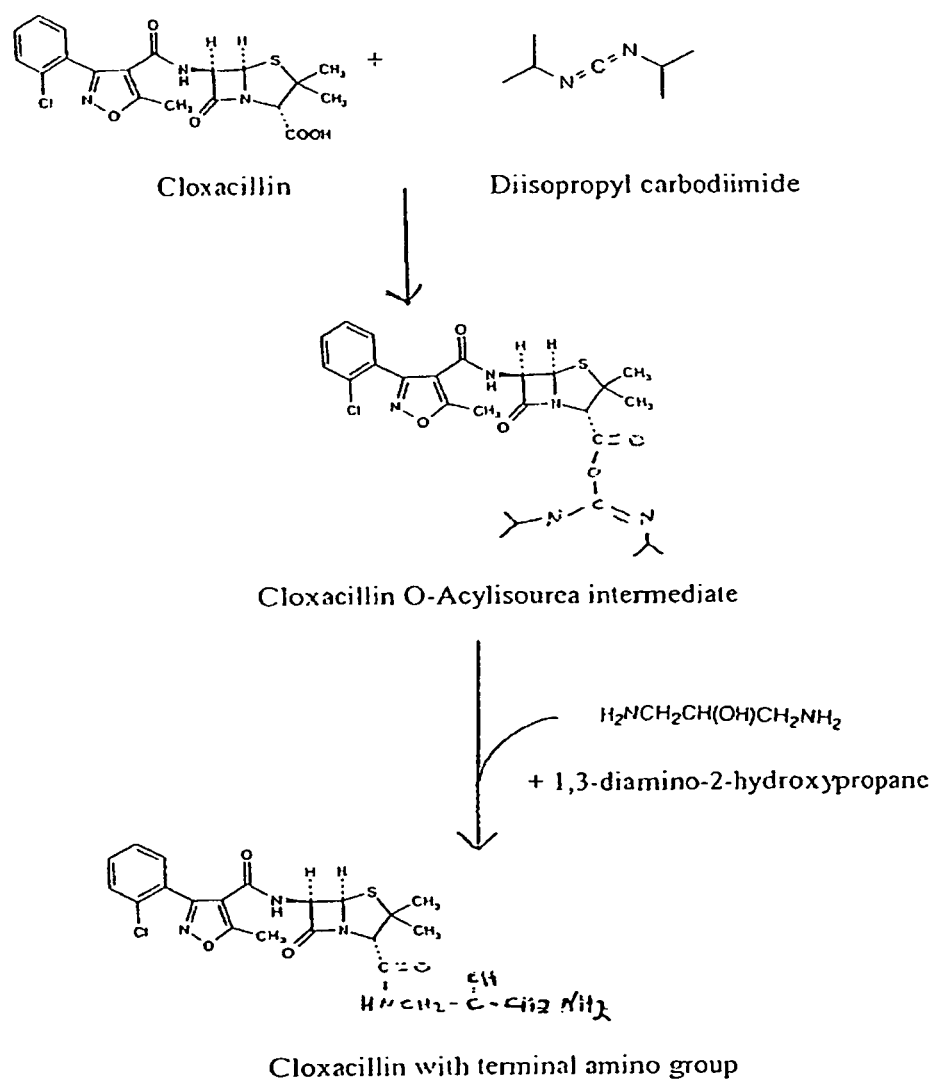
Figure 1: Conversion of cloxacillin to an aminocloxacillin derivative

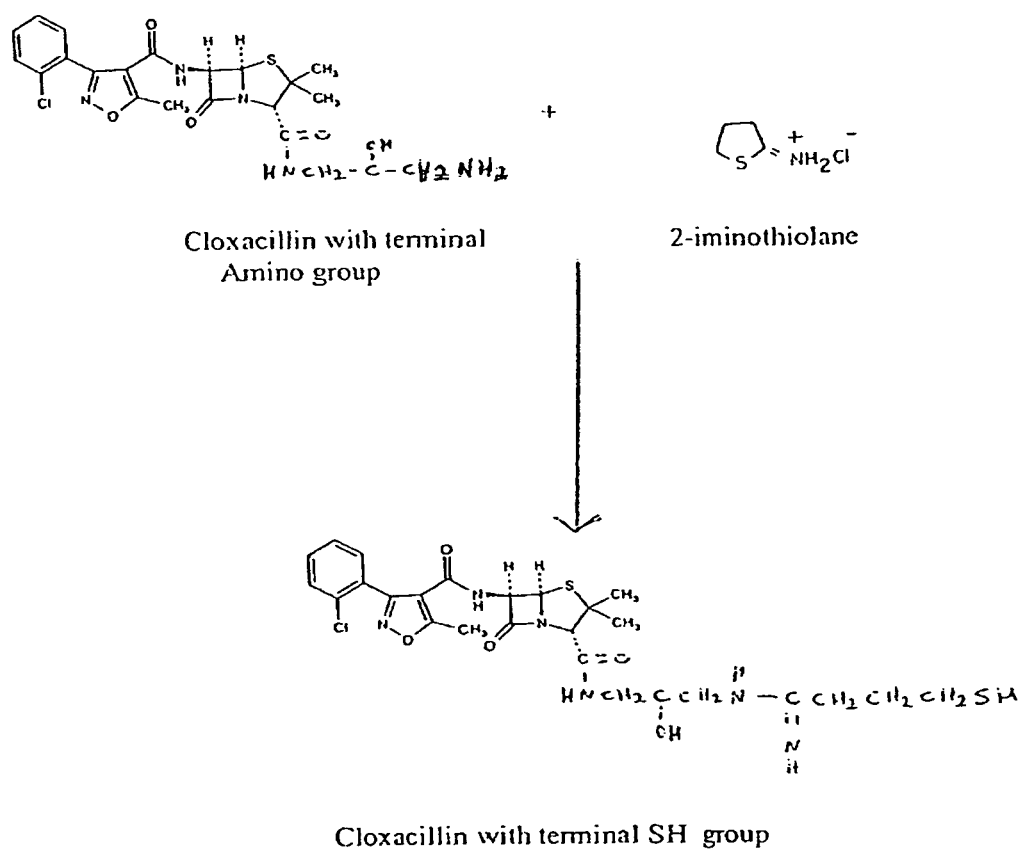
Figure 2: Conversion of cloxacillin with terminal amino group to Cloxacillin with terminal SH group
Cloxacillin with terminal Amino group
2-iminothiolane
Cloxacillin with terminal SH group

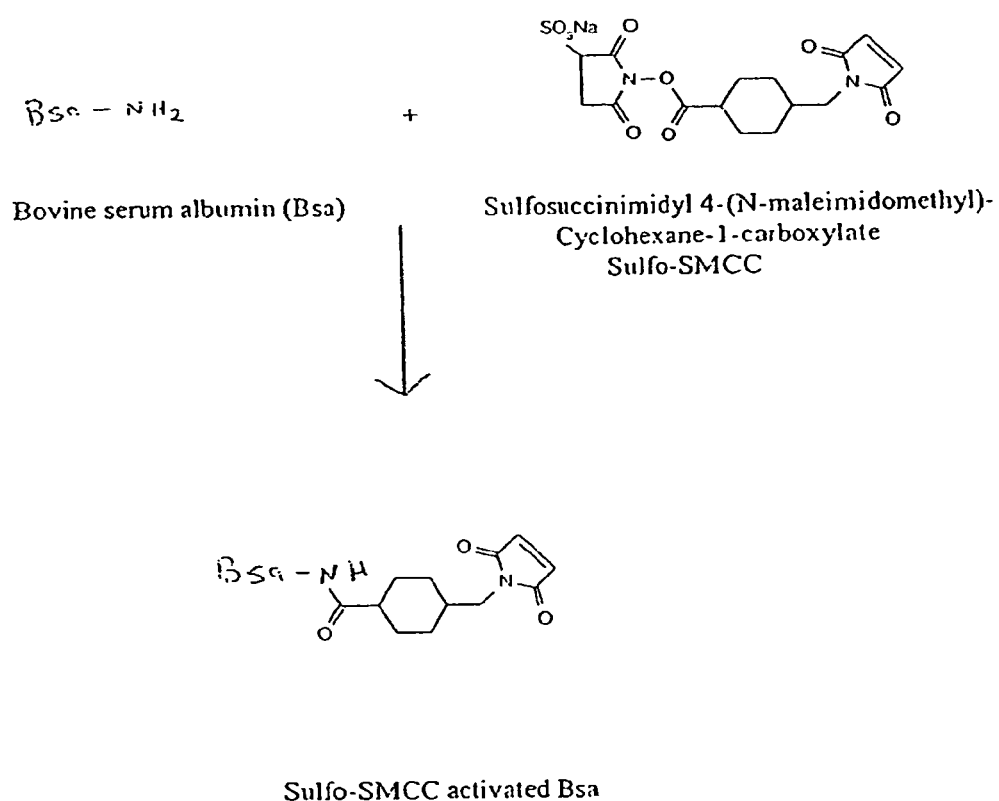

Figure 4: Maleimide-activated carrier protein reaction with SH terminal Cloxacillin to generate BSA-cloxacillin conjugate for spraying onto lateral flow test strip.

Sulfo-SMCC activated Bsa      Cloxacillin with terminal SH group

Bsa-cloxacillin conjugate

METHOD OF ATTACHING A LIGAND TO A SOLID SUPPORT

REFERENCE TO PRIOR APPLICATION

This is divisional application of application Ser. No. 10/289,089, filed Nov. 6, 2002 now abandoned. This application is based on and claims priority from U.S. Patent Application Ser. No. 60/332,877, filed Nov. 6, 2001, hereby incorporated by reference.

FIELD OF THE INVENTION

The invention relates to attaching small molecule ligands to a solid support, e.g., a lateral-flow test strip.

BACKGROUND OF THE INVENTION

Lateral-flow test strips for detecting one or more analytes in a fluid sample generally include a reagent, or ligand, immobilized within a defined region of the test strip, variously referred to as a detection zone, a test zone, and/or a control zone. The ligand of choice has binding affinity for another reagent in the mobile phase of the test strip. If the mobile-phase reagent is detectably labeled, a detectable signal is generated within the region of the test strip occupied by its immobilized binding partner. Lateral-flow test devices generating visible signals are well known in the art. Examples of such devices are described in U.S. Pat. Nos. 5,985,675, issued Nov. 16, 1999, and 6,319,466, issued Nov. 20, 2001, the teachings of which are incorporated herein by this reference.

Lateral-flow test strips are widely used in the food products industry. For example, the United States Food and Drug Administration (FDA) requires that bulk milk tankers be tested for presence of unsafe levels of beta-lactam antibiotics. The sensitivity required pursuant to Appendix N of the Pasteurized Milk Ordinance, in parts per billion, is: amoxicillin 10 ppb, ampicillin 10 ppb, penicillin G 5 ppb, ceftiofur 50 ppb, cephapirin 20 ppb, and cloxacillin 10 ppb (the "safe levels"). The FDA also requires that the results of such tests be automatically (electronically) analyzed and recorded. It is desirable, therefore, to provide milk-testing personnel with a user-friendly test strip that can be analyzed with or without an optical reader. The test strip is used to detect beta-lactams, including five or six of the following beta-lactams at or below safe level: penicillin G, amoxicillin, ampicillin, ceftiofur, cloxacillin and cephapirin.

The sensitivity of a test device or method relative to a particular analyte initially relates to the binding affinity between the analyte and the receptor. If the receptor and analyte have good affinity, analyte-receptor complex will form readily. In the case of a multianalyte receptor, the affinity of certain analytes to the receptor may be different than others, and may not reflect the desired detection level for one or more of the analytes requiring detection. In those cases, it is desired to adjust the test sensitivity to the particular analyte. For example, U.S. Pat. No. 6,319,466 describes a test device for detecting analytes at reduced sensitivity levels. It may also be necessary to increase the sensitivity of the test to a particular analyte above the sensitivity of the multianalyte receptor.

It is an object of this invention to provide test strips with improved test zone development for use with or without an optical reading device, such as a spectrophotometer. When using an optical reading device, such improvement may involve providing consistent and uniform color development in well-defined regions of the test strip, such as test zones and control zones, for easy interpretation of results.

Various mechanisms to improve color development in test strips include adding substances to increase the viscosity of the spray solution, such as sugars, for example, sucrose, or proteins, such as bovine serum albumin (BSA). Another method is to pretreat the receptor application area. Still another method for improving the quality of the test zone is to add an abundance of label, for example, gold sol. In the case of gold, the amount used is limited by the necessity of rapid, consistent flow through the porous test strip. A high percentage of gold in the spray solution may clog pores and inhibit flow.

The above-described limitation on the use of gold is more pronounced when a second test zone is employed, for example, a second test zone for cloxacillin. In the case of a single test zone, if conjugate attachment is inefficient, or test zone development is otherwise inadequate, it may be possible to increase the concentration of label, for example gold sol, to overcome the problem. Adding a second test zone to a test strip presents special challenges when trying to optimize signal development for each zone. If there is a second test zone, which would require a second gold sol label, the technique of adding additional gold label to improve line quality is limited.

SUMMARY OF THE INVENTION

The methods of the invention are particularly useful for immobilizing small molecule ligands having a free carboxyl group to a lateral-flow test strip via an attachment protein, in order to make a detection zone on the test strip that exhibits a clear signal and enhanced sensitivity. Accordingly, the invention features a method of attaching a ligand to a solid support, the method including the steps of (a) providing a ligand, the ligand having a free carboxyl group; (b) adding an amino group to the ligand to form a ligand-amino derivative; (c) converting the ligand amino derivative to a ligand sulfhydryl derivative; (d) joining the ligand sulfhydryl derivative to a protein to form a ligand-linker-protein conjugate; and (e) applying the ligand-linker-protein conjugate to the solid support.

Preferably, the ligand is a small molecule ligand having a free carboxyl group, which is bound to a solid support with the use of an attachment protein. The method is also useful for attaching small molecule ligands to a solid support by derivatizing the ligand to a carboxyl derivative, and then using the carboxyl-group and a linker, or spacer (as described below), to form a conjugate between the ligand and an attachment protein. A small molecule ligand suitable for the method of the invention can be, without limitation, an antibiotic having an exposed carboxyl group, for example, cloxicillin, cephalothin, cephradine, ceftiofur, amoxicillin, ampicillin, and carboxyl-terminated forms of penicillin, e.g., penicillin N and penicillin O, and quinolones, e.g., enrofloxicin. The method of the invention is suitable for additional antibiotics that, although not naturally possessing a terminal carboxyl group, can be, or have been, converted to an acid form; examples of antibiotics that can be attached to a solid support after being converted to an acid form include, without limitation, acid derivatives of tetracycline, acid derivatives of sulfonamides, succinate derivatives, e.g., chloramphenicol succinate, and oxime derivatives. Other small molecule ligands suitable for the method of the invention include, e.g., aflatoxins. The aflatoxin is converted to an oxime derivative, which includes a terminal carboxyl group, and is then attached to an attachment protein, as described below.

In the invention, ligands are immobilized to a solid support with the use of an attachment protein. The attachment protein serves as an anchor, to make the small molecule ligand bind to the support via the attachment protein. One theory behind the invention is that a small molecule ligand, attached to a protein to form a ligand-protein conjugate alters the conformation of the protein, and decreases the extent of attachment of the protein to the support. Accordingly, the invention provides a ligand-linker-protein conjugate with an improved propensity to attach to the solid support. Suitable attachment proteins are known to those skilled in the art to be proteins that bind readily to solid supports, such as, e.g., supports that include nitrocellulose, or that include polyethylene, such as a polyethylene membrane, for example POREX® (POREX is a registered trademark of Porex Technologies Corp. of Fairburn Ga.) membrane. An attachment protein for use in the invention can be, e.g., a carrier protein, i.e., a protein commonly used in conjunction with an immunogen, such as, without limitation, an albumin, e.g., bovine serum albumin (BSA). In another embodiment, the attachment protein is a protein that is rich in amino groups. The attachment protein can also be a protein that is relatively water soluble. Other examples of suitable attachment proteins are described below.

In another aspect, the invention includes adding an amino group to the ligand to form a ligand-amino derivative. Preferably, the adding step includes activating the carboxyl group to form a ligand reactive species, and adding the amino group to said ligand reactive species to form said ligand amino derivative. The activation can include reacting said carboxyl group with a zero-length cross linker. Activation can be done by reacting the carboxyl group with a carbodiimide. Alternatively, activation can be done by reacting the carboxyl group with a carbodiimide in the presence of N-hydroxysuccinimide (an NHS ester). Activation can be done by reacting said carboxyl group with a carbonylating compound. In one embodiment, the amino group is added via a diamine, e.g., 1,3-diamino-2-hydroxypropane.

In yet another aspect, the invention includes converting the ligand amino derivative to a ligand sulfhydryl derivative, e.g., by thiolation. Without limitation, thiolation can include the use of a thio-containing imidoester, or the use of S-acetylmercaptosuccinic anhydride, or the use of a thiol-containing succinimidyl derivative.

In a further aspect, the invention includes joining the ligand sulfhydryl derivative to a protein to form a ligand-linker-protein conjugate. The ligand is attached to the protein by, e.g., reacting said protein with a heterobifunctional cross-linking reagent to form said linker-protein conjugate, and reacting said linker-protein conjugate with said ligand sulfhydryl derivative. The heterobifunctional cross-linking reagent can be an amino and sulfhydryl group directed bifunctional reagent. For example, the heterobifunctional cross-linking reagent can include at one end a maleimide, e.g., sulfosuccinimidyl 4-(N-maleimidomethyl)-cyclohexane-1-carboxylate. The heterobifunctional reagent can include at one end an NHS ester. In another aspect, the invention features a method of attaching a ligand to a solid support by (a) providing a ligand having a free carboxyl group; (b) adding an amino group to said ligand to form a ligand-amino derivative; (c) joining the ligand amino derivative to a protein having a free amino group through an amino group directed homobifunctional cross-linker, to form a ligand-spacer-protein conjugate; and (d) applying the ligand-spacer-protein conjugate to the solid support. The adding step can include activating the carboxyl group to form a ligand reactive species, and adding said amino derivative to said ligand reactive species to form said ligand amino derivative. The amino group directed homobifunctional cross-linker can be an NHS ester, or a sulfo-NHS ester, cross-linking reagent.

In other aspects, the invention features (a) a lateral-flow test strip that includes a small molecule ligand attached by the methods described herein; (b) a microarray prepared from a solid support, such as nitrocellulose or polyethylene membrane, and includes a small molecule ligand attached by the methods described herein.

One aspect of achieving uniform and consistent test zone development is efficient attachment of the conjugate to the nitrocellulose. Another aspect of uniform and consistent test zone development is optimizing the conformation of the test zone conjugate so that it both attaches consistently to the nitrocellulose and maximizes the availability of the receptor-binding portion to the receptor. It is desirable to maximize the percentage of the conjugate that attaches to the nitrocellulose and assure even spacing across the test zone. At the same time, the capture portion of the binder conjugate molecule must remain readily available for binding unbound labeled receptor. If attachment to the nitrocellulose is inefficient and non-uniform, then some conjugate may remain unattached to the nitrocellulose. The unattached conjugate will interfere by competing with attached conjugate for binding to the labeled receptor. That is, some receptor that would otherwise bind in a clearly defined area will either bind in a poorly defined or wider area, or not at all, resulting in diffuse and generally poor, test zone development. Such a poor test zone is a problem whether or not an instrument, such as a reflectance reader, for example, a spectrophotometer, is used to analyze the results of a test. The problem, however, is more acute when reflectance reading is used to read and analyze test results. It is, therefore, an object of this invention to improve the quality of the test zone. We have found that adding a spacer linkage improves test zone quality.

The invention relates to an analyte or chemical residue test device and method for detecting an analyte or residue in a sample, particularly a liquid sample or extract. Often a liquid, such as milk, contains one or more contaminants or analytes that need to be detected. To do so, the present invention employs a binding protein, for example, a receptor, enzyme, or antibody, that binds with the analyte to form an analyte-receptor complex. The analyte-receptor complex can be detected through various methods, including labeling the receptor with a visible label, such as gold sol, for capture on a test line or test zone.

In one embodiment, a labeled beta-lactam binding protein, unlabeled antibodies to ceftiofur, ampicillin and cephapirin, and labeled antibodies to cloxacillin are combined in a solution and applied, for example, by spraying, onto a porous surface. When exposed to a sample, for example of fluid milk, the antibodies and the binding protein bind to their related analytes to form receptor-analyte complexes. Unlabeled antibody reduces the amount of related analyte available to bind to the labeled binding protein, decreasing test sensitivity to that analyte. Similarly, labeled antibody will bind its related analyte thereby increasing test sensitivity to the analyte, above that of the binding protein alone. In the specific example of detecting beta-lactams in fluid milk, a labeled antibody to cloxacillin binds cloxacillin from the sample preferentially to beta-lactam binding protein providing increased test sensitivity to cloxacillin. Lateral capillary flow occurs carrying the analyte-receptor complex, and any unbound labeled receptor, along a membrane, such as nitrocellulose, to one or more test lines or zones positioned on the membrane.

The test zones on the membrane each contain a binder for capture of unbound receptor. An example of such a binder is, for example, representative analyte conjugate, or analog thereof, attached to the membrane in a distinct area. In one embodiment, the analyte conjugate is, in a first line, a beta-lactam (other than a beta-lactam for which antibodies are provided) BSA conjugate, such as a ceforanide-BSA-conjugate. A second test zone contains cloxacillin-BSA conjugate for binding unbound, labeled cloxacillin antibody. The unbound labeled beta-lactam binding protein or unbound labeled cloxacillin antibody are captured by the related test zone conjugate and, as a result of the label, generate a signal visible to the eye or readable with an instrument.

In a typical lateral-flow test assay system, a test zone is sprayed onto a solid support that has sufficient pore size to allow liquid to flow along the membrane, such as nitrocellulose. Particularly for an inhibition-type lateral-flow test, where detection of an analyte in a sample is desired at or above an established tolerance level, and more particularly, when results on a test zone are compared in intensity to a control zone, it is important to have consistent and uniform test zone development.

If a small molecule, such as an antibiotic, is to be attached to a membrane, such as nitrocellulose, a carrier protein may be required. Such carrier proteins include, for example, bovine serum albumin (BSA). The carrier protein is conjugated to the analyte and attached to the nitrocellulose in the test zone.

In one embodiment, the invention features a method of attaching a ligand that has a free carboxyl group to a solid support by adding an amino group to the ligand to form a ligand-amino derivative, converting the ligand amino derivative to a ligand sulfhydryl derivative, attaching the ligand sulfhydryl derivative to a protein to form a ligand-linker-protein conjugate, and applying the ligand-linker-protein conjugate to the solid support.

BRIEF DESCRIPTION OF THE DRAWINGS

FIG. 1 illustrates the conversion of cloxacillin to a cloxacillin amino derivative.

FIG. 2 illustrates the conversion of a cloxacillin amino derivative to a cloxacillin sulfhydryl derivative.

FIG. 3 illustrates the activation of a carrier protein (BSA) to a maleimide activated carrier protein and conversion to sulfo-SMCC activated BSA.

FIG. 4 illustrates the reaction of the maleimide activated carrier protein with the sulfhydryl terminal cloxacillin to generate BSA-cloxacillin conjugate for application to the cloxacillin test zone.

DETAILED DESCRIPTION OF THE INVENTION

To detect target analytes, the present invention employs one or more labeled receptors for one or more analytes. Such receptors can be specific for particular analytes, such as antibody receptors, or multianalyte receptors, such as a binding protein, for example, a beta-lactam binding protein isolated from *Bacillus stearothermophilus* or *Bacillus licheniformis*. Such labeled receptors react with the target analyte to form an analyte-receptor complex. Such receptors can also include, for example, enzymes; monoclonal antibodies and polyclonal antibodies. Generally, the molecular weight of an analyte will be between 100 and about 1,000. The present method can, however, also be applied to detect macro-molecules of a much higher molecular weight. Antigens, haptens and their antibodies, hormones, vitamins, drugs, metabolites and their receptors and binding materials, fungicides, herbicides, pesticides, plant, animal and microbial toxins, may be determined using the present method. Other analytes determinable by the methods and devices of the present invention include antibiotics, such as beta-lactams, cephalosporins, erythromycin, sulfonamides, tetracyclines, nitrofurans, quinolones, vancomycin, gentamicin, amikacin, chloramphenicol, streptomycin and tobramycin and toxins, such as mycotoxins, such as aflatoxin and vomitoxin and drugs of abuse, such as opioids and the like, as well as the metabolites thereof.

Figure 6:
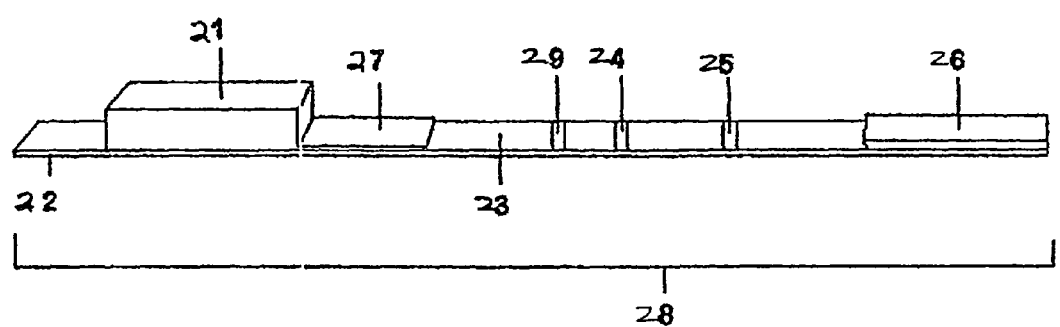
FIG. 6 is a perspective view of another test strip embodiment of the invention.

FIG. 6 is a perspective view of the test strip used in one embodiment. The test device includes a support strip 22 and a sample-absorbing matrix 21. The sample-absorbing matrix 21 comprises a material for absorbing an amount of the sample, and filtering unwanted substances out of the sample, for example, a sponge. The test device also includes a mobile-phase support 27 attached to the support strip 22 and in contact with the sample-absorbing matrix 21. A mobile-phase composition is disposed within or on the mobile-phase support 27 and has one or more labeled receptors for binding with the analyte or analytes of interest. The mobile-phase composition can be carried in the sample flow together with the sample. A stationary-phase membrane 23 has a first membrane end in contact with the mobile-phase support 27 and a second membrane end in contact with the disposal zone 26. The membrane allows lateral capillary flow of the sample from the first membrane end to the second membrane end. A first test zone 29 and optionally a second test zone 24 are on the stationary phase membrane 23 between the first membrane and the second membrane end. The test zones 24, 29 contain binders, typically representative analytes, or analogues thereof, which capture unbound labeled receptor. A control zone 25 is also on the stationary phase membrane 23 between the test zones 24, 29 and second membrane end. The control zone 25 contains receptors for the analyte receptors, for example, an antibody to the particular receptor, for binding with both analyte bound receptor and excess unbound receptor. Additional control zones are also possible, for example, corresponding to the number of test zones.

For multianalyte detection, multiple receptors may be employed. Typical receptors include macromolecules, such as monoclonal or polyclonal antibodies, hormone receptors and enzymes and synthetic receptors such as those generated through molecular imprinting of synthetic polymers or molecular imprinting inside dendrimers. Each particular receptor generally requires a related test zone. Some receptors, such as the beta-lactam binding protein, are sensitive to multiple analytes so require only a single detection zone for multi-analyte detection. If additional labeled receptors, such as antibodies, are used, additional test zones may be required.

Different labels may be employed including colloidal gold particles. Other particles useful in the practice of the invention include, but are not limited to, colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles, colloidal metal ferrite particles, any of the above-mentioned colloidal particles coated with an organic or inorganic layer; protein or peptide molecules; liposomes; or organic polymer latex particles, such as polystyrene latex beads. Other labels may also be used including, but not limited to, luminescent labels; fluorescent labels; or chemical labels, such as electroactive agents (e.g., ferrocyanide); enzymes; radioactive labels; or radiofrequency labels.

In a particular embodiment, the label is colloidal gold particles. The size of the particles may be related to porosity of the membrane strip; the particles are preferably sufficiently small to be transported along the membrane by capillary action of fluid. The number of particles present in the test strip may vary, depending on the size and composition of the test strip, and the desired level of sensitivity of the assay. Using fewer particles is one method for increasing sensitivity of the test. If minimal particles are desired, it will be important to both optimize capture at the control and test zones and optimize conjugate attachment to the test strip, for example, by the methods of the herein described invention.

The test device includes a support strip and a sample-absorbing matrix. The sample-absorbing matrix comprises a material for absorbing an amount of the sample and filtering unwanted substances out of the sample, for example, a sponge. The test device also includes a mobile-phase support attached to the support strip and in contact with the sample-absorbing matrix. A mobile-phase composition is disposed within or on the mobile-phase support and has one or more labeled receptors for binding with the analyte or analytes of interest. The mobile-phase composition can be carried in the sample flow together with the sample. A stationary-phase support strip, which may be part of the same strip as the mobile-phase composition, or disposed on a separate strip in fluid flow contact with the first strip, has a first membrane end in contact with the mobile-phase composition and a second membrane end in contact with the disposal zone. The membrane allows lateral-capillary flow of the sample from the first membrane end to the second membrane end. One or more test zones are on the stationary-phase membrane between the first membrane and the second membrane end. The test zones contain binders, which are typically representative analytes or analogues thereof, which capture unbound labeled receptor. One or more optional control zones are also on the stationary-phase membrane between the test zone and second membrane end. The control zone contains receptor for the analyte receptor, for example, an antibody to the particular receptor, for binding with both analyte-bound receptor and excess unbound receptor.

In one embodiment, labeled receptors are applied to a membrane. Both the membrane and the absorbent sponge may serve as a filter to remove substances from milk, or other test fluids, which would either inhibit flow or interfere with other aspects of the test reaction. When exposed to the sample liquid, lateral capillary flow occurs thereon. The liquid flow carries the analyte-receptor complex and any unbound labeled receptor. Positioned on the membrane in the flow path are one or more test zones. Each test zone has, typically, a representative analyte conjugate attached to the membrane. The analyte conjugate captures unbound labeled receptor to form a first analyte conjugate receptor complex that, as a result of the label, has a signal visible to the eye or readable, in the manner described herein, with an instrument such as spectrophotometer.

In an embodiment of this invention, with two test zones, the first test zone, comprising a ceforanide-BSA conjugate, was made by using the amino group on the ceforanide to add a sulfhydryl group. Next a cross-linking agent, for example, Sulfosuccinimidyl-4-(N-maleimidomethyl)cyclohexane-1-carboxylate (sulfo-SMCC), was added to link the sulfhydryl group on the ceforanide derivative to the amino group on the carrier protein. However, the second test zone—the cloxacillin-BSA test zone—showed poor development at the desired detection level. For cloxacillin, the direct attachment method, through its carboxyl group via a carbodiimide cross-link, resulted in poor sensitivity. Adding an additional spacer linkage, between the carrier protein and the cloxacillin derivative, improved the quality of the test zone color development and, thereby, improved test sensitivity and accuracy.

In a particular embodiment (FIG. 1), a reagent having a free amino group, such as a diamine, for example, 1,3-diamino-2-hydroxypropane, was bound to cloxacillin. Before adding the diamine, the carboxyl (—COOH) group on cloxacillin was activated by a zero-length cross-linker (converting the carboxyl group to a reactive species). Examples of zero-length cross-linkers are well known in the art, for example, without limitation, carbodiimides, for example, 1-ethyl-3-(3-dimethylaminopropyl carbodiimide hydrochloride) (EDC), EDC plus N-hydroxysulfosuccinimide (sulfo-NHS), 1-cyclohexyl-3-(2-morpholinoethyl) carbodiimide (CMC), dicyclohexyl carbodiimide (DCC) or diisopropyl carbodiimide (DIC); N-ethyl-3-phenylisoxazolium-3'-sulfonate (Woodward's Reagent K); diethylpyrocarbonate; ethylchloroformate, N-ethylbenzisotazolium tetra fluorborate; N-carbalkoxydihydroquinoline; and N,N'-carbonyldiimidazole (CDI). Optionally, an N-hydroxysuccinimide ester can be included in the reaction with a carbodiimide to enhance the reaction. Alternatively, carbonylating compounds like N,N'-carbonyldiimidazole can be used as an alternative to a carbodiimide.

After the carboxyl group on the cloxacillin is converted to a cloxacillin intermediate reactive species, in one embodiment, a diamine was added to convert the cloxacillin intermediate to a cloxacillin amino derivative. Examples of diamines which can be used in such a reaction, depending on the particular needs, are 1,4-diamino-2-butanone, diaminoethylene, ethylene diamine, 1,1-diaminohexane, diaminodipropylamine, 1,3-diaminopropane, 1,3-diamino-2-hydroxypropane and 1,4-diaminobutane, Choice of diamines are controlled partly by the importance of avoiding steric hindrance at the binding end and partly by conformation changes of the carrier protein which may negatively impact consistent, predictable binding to the nitrocellulose.

In FIG. 2, the free amino group on the cloxacillin amino derivative is converted to a sulfhydryl group by thiolation with thiol-containing imidoesters, for example, Traut's Reagent. Other useful methods for converting an amino group to a sulfhydryl group include thiolation with S-acetylmercaptosuccinic anhydride, thiolation with thiol-containing succinimidyl derivatives such as N-succinimidyl S-acetylthioacetate (SATA) and succinimidyl acetylthiopropionate (SATP) and thiolation with 3-(3-acetylthiopropionyl)thiazolidine-2-thione or 3-(3-p-methoxybenzylthiopropionyll)thiazolidine-2-thione.

After the sulfhydryl group is added to the cloxacillin, one method for conjugate synthesis is to use a heterobifunctional cross-linking reagent. The carrier protein is first reacted with a heterobifunctional cross-linking reagent (FIG. 3). For example, reacting BSA with the NHS ester of sulfosuccinimidyl 4-(N-maleimidomethyl)-cyclohexane-1-carboxylate (sulfo-SMCC). The succinimidyl group reacts with available amino groups on the carrier protein. The maleimide group is then available to react with the sulfhydryl group on the cloxacillin derivative. It is important to have the carrier protein free of any sulfhydryl groups and any free sulfhydryl groups on the carrier protein can be first blocked with N-ethylmaleimide. The sulfhydryl specific carrier protein derivative is then linked to the cloxacillin sulfhydryl derivative to form the cloxacillin-BSA conjugate (FIG. 4).

In other embodiments, other carrier proteins, such as ovalbumin (OVA) or keyhole limpet hemocyanin (KLH) can be substituted for BSA. Such carrier proteins react similarly with sulfo-SMCC to form a sulfo-SMCC activated carrier protein for reaction with the terminal SH group of the cloxacillin.

Other analytes with an available carboxyl group (carboxyl group not required in the principle binding reaction of the test) can be cross-linked in a similar manner. It is also possible to use the reverse of the above reaction by synthesizing cloxacillin-sulfo-SMCC for conjugation to a carrier protein containing sulfhydryl groups or a carrier protein derivative containing sulfhydryl group.

In embodiments in which the molecule to be bound to the test zone, such as a small molecule, for example, an aflatoxin, does not contain a free carboxyl group, the molecule can be derivatized, by methods well known in the art, to add a carboxyl group. For example, aflatoxin can be converted to its oxime derivative. One method is by dissolving alfatoxin $B_1$ in 1 ml dry ethanol and 1 ml dry DMSO, and incubating at 56° C., followed by incubating for 2-3 hours with carboxymethoxylamine hemihydrochloride dissolved in dry pyridine. The carboxyl group of the oxime derivative is converted to its intermediate reactive species via a zero-length cross-linker.

In another embodiment, conjugation of carrier protein to representative analyte is through a homobifunctional cross-linker between two amino groups. Examples of useful homobifunctional cross-linkers include NHS esters. NHS esters useful in the invention include, without limitation, disuccinimidyl suberate (DSS), disuccinimidyl tartarate (DST), NHS esters, such as 3,3'-dithiobis(succinimidylpropionate) (DSP, Lomant's reagent), 3,3'-Dithiobis(sulfosuccinimidylpropionate) (DTSSP), disuccinimidyl tartarate (DST), disulfosuccinimidyl tartarate (sulfo-DST), ethyleneglycol bis-(succinimidylsuccinate) (EGS), ethyleneglycol bis-(sulfosuccinimidylsuccinate) (sulfo-EGS), disuccinimidyl glutarate (DSG), and N,N'-disuccinimidyl carbonate (DSC).

Figure 5:
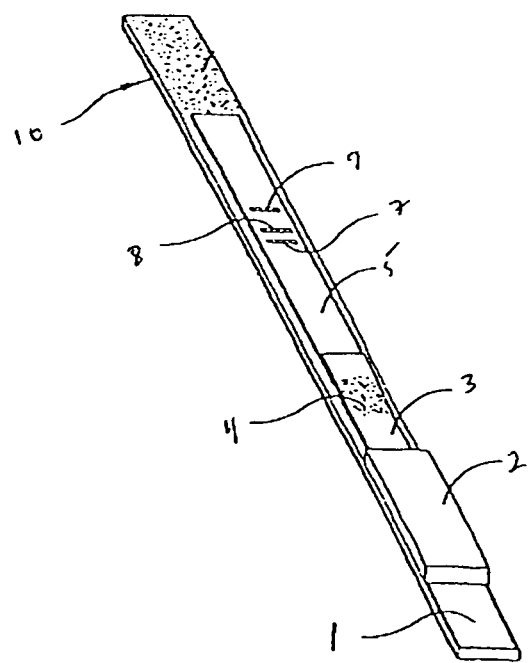
FIG. 5 is a perspective view of the test strip embodiment, illustrating finger hold area 1, created by positioning the sample pad 2 medially, and second test zone 8 for cloxacillin detection. The test strip is placed in an incubator set at 45 degrees Celsius. Sample is applied to sample pad 2. Sample flows off the sample pad 2 to the POREX® 3 containing unlabeled and labeled receptors 4. The receptors bind related small molecules from the sample forming a complex that flows down the strip through a porous membrane 5 and to the first test zones 7, and second test zone 8, and the control zone 9 and finally the disposal zone 10.

It is often the case, as is so in one of the embodiments of this invention, that a control zone, situated between the test zone and the second end of the test strip of FIG. 5, is used for comparison of the signal in the test zone. The control zones typically comprise an antibody to the receptor. The antibody captures both labeled and unlabeled receptor, typically an antibody to the receptor. Labeled receptor captured at the control zone generates a signal that can be visible to the eye or readable with an instrument. In the preferred embodiment, if the signal in the test zone is more intense than the signal in the related control zone, the test indicates that the analyte is not present or is not present above the allowable level (a negative test). If the test zone signal is less intense than the related control zone signal, the test indicates that the analyte is present in an amount in excess of allowable levels (a positive test).

A control zone can generate a signal either on contact with sample or on contact with specific test material, such as labeled receptor, such as when the control zone contains an antibody to the particular receptor or, in the case of antibody receptors, an antibody binding protein, such as, for example, protein A, protein G, recombinant protein A, recombinant protein G, recombinant protein AG.

In many of the described embodiments an optical reader will be required to distinguish between one or more test zones and one or more control zones. Particularly when using a reader, consistent, uniform and clearly defined test and control zone color development is important. As such, techniques previously described for improving the quality of the test zone, such as with a spacer linkage, provides maximum flexibility. In one embodiment, the method employs a lateral-flow test strip in combination with a reflectance reader.

In a particular embodiment, two or more test zones are utilized. Such test zones can each have a separate control zone generating two control zone values or, preferably, one control zone resulting in one control value to be used for comparison to both test zones.

In another particular embodiment, one test zone contains binder to capture unbound labeled beta-lactam multianalyte receptor and another test zone contains binder for unbound labeled specific receptor, for example, anti-cloxacillin receptor. In this embodiment, a single control zone is compared first to one test zone and then to the other test zone. More binding in the control zone relative to the test zone reflects a positive result.

Depending on the particular embodiment, a positive result in one test zone and negative result in the other test zone discloses the presence of the one or more analytes detected in the particular test zone. In a particular embodiment, a positive result informs the user only that the test is positive for a family of drugs, such as beta-lactams, but allows no further conclusion.

Although the embodiments described above focus on single service test devices, it will be appreciated that the herein described method has wide applicability. For example, binding of capture reagents to microarrays, particularly protein microarrays, must be accurate and consistent while maintaining the capturing capacity of the capture reagent. The described spacer linkage method can be used to optimize binding of carrier proteins and target analytes to such microarrays while maintaining or improving the capturing capacity of the capture reagent.

EXAMPLE

The invention will now be described by the following example:

Lateral-Flow Test for Six Beta-Lactams in Milk at Safe Level

The three-line test for detection of penicillin-G, amoxicillin, ampicillin, cloxacillin, ceftiofur and cephaparin at safe level consists of two test zones and one control zone.

The first test zone solution, consisting of a ceforanide-BSA conjugate at 2-4 mg/ml in 10 mM sodium phosphate, pH 6.9, containing 8% sucrose, 2-6 mg/ml BSA, 0.01% BIO-TERGE® (BIO-TERGE is a registered trademark of StepHan Chemical company of Northfield, Ill.) and PROCLIN®5000 (155 µl/L) (PROCLINE is a registered trademark of Rohm and Haas Company of Philadelphia, Pa.) was sprayed onto nitrocellulose using a BIODOT® sprayer. The mixture was sprayed 1.6 cm above the bottom edge of the nitrocellulose at a rate of 0.8 µl/cm.

To make the second test zone solution, 1 g of cloxacillin was dissolved in approximately ml anhydrous DMSO. Further, 500 mg of N-hydroxysulfosuccimide was dissolved in anhydrous DMSO. We then combined both solutions and added 0.5 ml of Diisopropyl carbodiimide. The reaction proceeded for 2 hours. We then dissolved 2 g of 1,3 diamino hydroxypropane in 0.05 M phosphate buffer and brought the solution to pH 7.4. We added the activated cloxacillin solution and let the reaction proceed for 2 days (FIG. 1). We purified the amino-cloxacillin derivative on a C-18 extraction column. We then took 171 mg of the amino-cloxacillin derivative and dissolved it in 0.16 M borate-phosphate buffer, pH 8.0, containing 2 mM EDTA. We added 43 mg 2-iminothiolane and monitored the formation of the cloxacillin-SH derivative by HPLC. We then cooled the solution and brought it to pH 7.0 with 0.4 M phosphate buffer, pH 6.5 (FIG. 2).

BSA was activated by adding 136.4 mg of S-SMCC in 0.16 M borate-phosphate buffer, pH 8.0, containing 2 mM EDTA (FIG. 3). The reaction proceeded for 2 hours and then cooled and brought the solution to pH 7.0 with 0.4 Phosphate buffer, pH 6.5. We then added the cloxacillin-SH solution to the maleimide activated BSA and let it react at 4° C. for at least 24 hours to generate the cloxacillin-BSA conjugate (FIG. 4). We then purified the cloxacillin-BSA conjugate to remove free drug.

The carboxyl group of cloxacillin was modified to a primary amino derivative by diamines which have two available primary groups for subsequent reactions. One primary amino group was reacted with the activated cloxacillin carboxyl group, such as the N-hydroxysulfosuccinimide ester, to form a covalent amide linkage between the spacer and the cloxacillin. The other end of the spacer now attached to cloxacillin has an available primary amino group for further reaction to the carrier protein, which will in turn be bound to the nitrocellulose.

For spraying onto nitrocellulose, the BSA-cloxacillin conjugate was diluted to less than 0.5 mg/ml in 10 mM sodium phosphate buffer, pH 6.9, containing 8% sucrose and 15-25 mg/ml BSA. The solution was sprayed onto the nitrocellulose as a second test zone for binding free anti-cloxacillin antibody tracer. The BSA-ceforanide conjugate was diluted to 2-4 mg/ml in 10 mM sodium phosphate buffer, pH 6.9, containing 8% sucrose and 4 mg/ml BSA. That solution was sprayed as the first test zone for binding free, labeled β-lactam binding protein. In general, there is leeway in the amount of additives and type of additives added to the conjugate spray solutions to generate a high quality test zone.

The control zone solution consists of a mixture of 8-15% of rabbit anti β-lactam receptor and 1.5-2.5% rabbit anti-cloxacillin antibody. The solution was buffered with 10 mM sodium phosphate, pH 7.2, containing 4% sucrose, 2 mg/ml BSA, 0.01% BIO-TERGE® and 0.01% PROCLIN 5000®. It was sprayed 2.8 cm above the bottom edge of the nitrocellulose at a rate of 0.9 µl/cm.

The gold label consists of a combination of a β-lactam receptor gold bead and a monoclonal anti-cloxacillin gold bead. Approximately 30% of the solution consists of beads coated with 600 U (units) of purified β-lactam receptor and approximately 20% consisted of gold beads coated with 450 U of purified anti-cloxacillin antibody. To the remainder of the solution was added a 10 mM sodium phosphate buffer pH 7.4, containing 40% sucrose and 10% BSA. The combined bead solution was sprayed at 0.7 to 0.9 µl/cm with 2 to 4 passes onto POREX®.

The monoclonal to cloxacillin was purified by ammonium sulfate precipitation at 50% saturation and dialyzed against 20 mM sodium phosphate buffer, pH 7.2, containing 50 mM sodium chloride.

The rabbit anti-cloxacillin antibody was made by using the purified cloxacillin monoclonal antibody as the immunogen. The rabbit anti-cloxacillin was purified by affinity chromatography and desalted against 20 mM sodium phosphate buffer, pH 7.2, containing 50 mM sodium chloride.

The invention claimed is:

1. A lateral-flow test method for detecting one or more analytes in a test sample, the method comprising:
(a) adding the test sample to a lateral flow test strip, the test strip including a test zone binder with affinity for an unbound labeled analyte receptor, the test strip comprising a test zone and a control zone in a spaced apart configuration on the test strip;
(b) allowing the sample to contact the unbound labeled receptor, the unbound labeled receptor having affinity to an analyte to be detected so that the unbound labeled receptor reacts with the analyte to form analyte bound labeled receptor;
(c) subsequent to allowing the sample to contact the unbound labeled receptor, allowing the unbound labeled receptor to come in contact with the test zone binder, the test zone binder having affinity to unbound labeled receptor but not the analyte bound labeled receptor, wherein when the unbound labeled receptor reacts with the test zone binder a visible signal can be detected in the test zone; and
(d) detecting the visible signal in the test zone,
wherein the test is negative for the detection of the one or more analytes when the signal from the test zone is more intense than the signal in the control zone and the test is positive for the one or more analytes when the signal from the control zone is more intense than the signal from the test zone, and characterized in that the test zone binder is attached to the test strip through a spacer linkage to a protein and wherein the protein is attached to both the test strip and the spacer linkage.

2. The method of claim 1, wherein the unbound labeled receptor is applied to a first area on the test strip, said first area being spaced apart from the test zone, before said unbound labeled receptor is allowed to react with the one or more analytes in the test sample.

3. The method of claim 1, wherein an optical reader is used to detect the visible signal and provide the result.

4. The method of claim 1, further comprising contacting an unlabeled receptor with the sample and allowing the unlabeled receptor to react with an analyte.

5. The method of claim 1, wherein the visible signal is a color change and a reader measures a reflectance difference between the control zone signal and the test zone signal to indicate the presence or absence of the one or more analytes within the sample.

6. The method of claim 1, further comprising a test for multiple analytes characterized by a plurality of labeled receptors and a plurality of test zone binders.

7. The method of claim 6, further comprising a plurality of test zones each containing a different test zone binder for each of the plurality of labeled receptors.

8. The method of claim 1, further comprising combining one or more unlabeled receptors with the unbound labeled receptor and the sample, said combining occurring prior to allowing the unbound labeled receptor to come in contact with the test zone binder.

9. The method of claim 8, wherein the unlabeled receptors do not bind to test zone binders.

10. The method of claim 1, wherein said test strip comprises nitrocellulose.

11. The method of claim 1, wherein said test strip comprises polyethylene.

12. A lateral-flow test method for detecting one or more analytes in a test sample, the method comprising:
(a) attaching to a lateral flow test strip, through a spacer linkage to a protein a test zone binder with affinity for unbound labeled analyte receptor, said attaching through a spacer linkage comprising: (i) providing the test zone binder, said test zone binder having a free carboxyl group; (ii) adding an amino group to said test zone binder to form a test zone binder-amino derivative; (iii) converting said test zone binder-amino derivative to a test zone binder-sulfhydryl derivative; (iv) joining said test zone binder-sulfhydryl derivative to the protein to form a test zone binder-spacer linkage-protein conjugate;

(b) applying said test zone binder-spacer linkage-protein conjugate to said test strip;

(c) contacting the sample with the unbound labeled analyte receptor, the unbound labeled analyte receptor having affinity to at least one analyte;

(d) allowing the unbound labeled receptor to react with the analyte to form a bound labeled receptor;

(e) subsequent to contacting the sample with the unbound labeled receptor, contacting the unbound labeled receptor with the test zone binder, the test zone binder having affinity to the unbound labeled receptor but not the bound labeled receptor, wherein at least a portion of the unbound labeled receptor will react with the test zone binder generating a visible signal in the test zone that can be detected; and (f) detecting the visible signal in the test zone, wherein the test is negative for the detection of the one or more analytes when the signal from test zone is more intense than the signal in a control zone, the control zone located on the test strip in a spaced apart relationship with the test zone, and the test is positive for one or more analytes when the signal from a control zone is more intense than the signal from the test zone.

13. The method of claim 12 wherein said test zone binder is a small molecule binder.

14. The method of claim 12 wherein said test zone binder is an antibiotic.

15. The method of claim 14 wherein said test zone binder is cloxacillin.

16. The method of claim 12 wherein said protein is a carrier protein.

17. The method of claim 12 wherein said protein is an albumin.

18. The method of claim 12 wherein said protein is bovine serum albumin (BSA).

19. The method of claim 12, wherein said adding an amino group comprises activating said carboxyl group to form a binder reactive species, and adding said amino group to said binder reactive species to form said binder amino derivative.

20. The method of claim 19, wherein said activating comprises reacting said carboxyl group with a zero-length cross linker.

21. The method of claim 19, wherein said activating comprises reacting said carboxyl group with a carbodiimide.

22. The method of claim 19, wherein said activating is in the presence of an N-hydroxysuccinimide ester.

23. The method of claim 19, wherein said activating comprises reacting said carboxyl group with a carbonylating compound.

24. The method of claim 12, wherein said amino group is a diamine.

25. The method of claim 24, wherein said diamine is 1,3-diamino-2-hydroxypropane.

26. The method of claim 24, wherein said diamine is selected from the group consisting of 1,4-diamino-2-butanone, diaminoethylene, ethylene diamine, 1,1-diaminohexane, diaminodipropylamine, 1,3-diaminopropane, 1,3-diamino-2-hydroxypropane, and 1,4-diaminobutane.

27. The method of claim 12, wherein said converting step comprises thiolation.

28. The method of claim 27, wherein said thiolation comprises the use of a thio-containing imidoester.

29. The method of claim 27, wherein said thiolation comprises the use of S-acetylmercaptosuccinic anhydride.

30. The method of claim 27, wherein said thiolation comprises the use of a thiol-containing succinimidyl derivative.

31. The method of claim 27, wherein said thiolation comprises the use of a compound selected from the group consisting of 3-(3-acetylthiopropionyl)thiazolidine-2-thione and 3-(3-p-methoxybenzylthiopropionyll)thiazolidine-2-thione.

32. The method of claim 12, wherein said joining comprises reacting said protein with a heterobifunctional cross-linking reagent to form said spacer linkage-protein conjugate, and reacting said spacer linkage-protein conjugate with said binder sulfhydryl derivative.

33. The method of claim 32, wherein said heterobifunctional cross-linking reagent comprises an amino and sulfhydryl group directed bifunctional reagent.

34. The method of claim 32, wherein said heterobifunctional cross-linking reagent comprises a maleimide and a NHS ester.

35. The method of claim 32, wherein said heterobifunctional cross-linking reagent is sulfosuccinimidyl 4-(N-maleimidomethyl)-cyclohexane-1-carboxylate.

36. A lateral-flow test method for detecting one or more analytes in a test sample, the method comprising:

(a) attaching a test zone binder with affinity for unbound labeled analyte receptor to a test zone on a lateral flow test strip, said attaching comprising: (i) providing a test zone binder having a free carboxyl group; (ii) adding an amino group to said test zone binder to form a binder-amino derivative; (iii) joining said test zone binder amino derivative to a protein having a free amino group, through an amino group directed homobifunctional cross-linker, to form a test zone binder-spacer linkage-protein conjugate; and (iv) applying said test zone binder-spacer linkage-protein conjugate to said test strip;

(b) contacting the sample with the unbound labeled receptor, the unbound labeled receptor having affinity to at least one analyte to be detected;

(c) allowing the unbound labeled receptor to react with the analyte;

(d) contacting the unbound labeled receptor, previously allowed to react with the analyte, with the test zone binder, wherein a portion of the receptor, unbound to analyte from the sample, will react with the test zone binder in the test zone generating a visible result that can be detected;

(e) detecting the visible signal in the test zone, wherein the test is negative for the detection of the one or more analytes when the signal from the test zone is more intense than the signal in a control zone, the control zone located on the test strip in a spaced apart relationship with the test zone, and the test is positive for one or more analytes when the signal from the control zone is more intense than the signal from the test zone.

37. The method of claim 36, wherein said adding an amino group comprises activating said carboxyl group to form a test zone binder reactive species, and adding said amino group to said test zone binder reactive species to form said test zone binder amino derivative.

38. The method of claim 36, wherein said amino group directed homobifunctional cross-linker is a NHS ester reagent.

39. The method of claim 36, wherein said amino group directed homobifunctional cross-linker is a N-hydroxysuccinimide ester derivative reagent.

* * * * *